(12) United States Patent
Auguste et al.

(10) Patent No.: US 7,211,244 B2
(45) Date of Patent: *May 1, 2007

(54) MASCARA COMPRISING SOLID PARTICLES

(75) Inventors: Frédéric Auguste, Chevilly-Larue (FR); Florence Tournilhac, Paris (FR)

(73) Assignee: L'Oreal, S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/195,430

(22) Filed: Jul. 16, 2002

(65) Prior Publication Data

US 2003/0068290 A1    Apr. 10, 2003

Related U.S. Application Data

(60) Provisional application No. 60/306,431, filed on Jul. 20, 2001.

(30) Foreign Application Priority Data

Jul. 16, 2001    (FR) .................................. 01 09502

(51) Int. Cl.
*A61Q 1/10* (2006.01)
*A61Q 5/00* (2006.01)

(52) U.S. Cl. ................. 424/70.7; 424/70.1; 424/70.22; 424/70.13; 424/70.16; 424/401

(58) Field of Classification Search ................ 424/401, 424/70.7
See application file for complete search history.

(56) References Cited

U.S. PATENT DOCUMENTS

| | | | |
|---|---|---|---|
| 3,937,811 A | | 2/1976 | Papantoniou et al. |
| 5,389,363 A | * | 2/1995 | Snyder et al. ............. 424/70.7 |
| 5,660,818 A | | 8/1997 | Dubief et al. |
| 5,720,943 A | | 2/1998 | Mougin et al. |
| 5,849,278 A | | 12/1998 | Piot et al. |
| 5,851,517 A | | 12/1998 | Mougin et al. |
| 5,858,338 A | | 1/1999 | Piot et al. |
| 5,945,095 A | | 8/1999 | Mougin et al. |
| 5,961,989 A | | 10/1999 | Mougin et al. |
| 6,001,168 A | | 12/1999 | Hall-Goulle et al. |
| 6,254,877 B1 | | 7/2001 | De La Poterie et al. |
| 6,264,933 B1 | | 7/2001 | Bodelin et al. |
| 6,274,131 B1 | | 8/2001 | Piot et al. |
| 6,372,201 B1 | | 4/2002 | Leuridan et al. |
| 6,491,931 B1 | * | 12/2002 | Collin ....................... 424/401 |
| 6,682,748 B1 | * | 1/2004 | De La Poterie et al. .... 424/401 |
| 2001/0006665 A1 | | 7/2001 | Auguste |
| 2002/0085986 A1 | | 7/2002 | de la Poterie et al. |
| 2004/0009201 A1 | | 1/2004 | Collin et al. |

FOREIGN PATENT DOCUMENTS

| | | |
|---|---|---|
| EP | 0 557 196 | 8/1993 |
| EP | 0 847 752 | 6/1998 |
| EP | 0 923 928 | 6/1999 |
| EP | 1 040 814 | 10/2000 |
| EP | 1 048 282 | 11/2000 |
| EP | 1 064 920 | 1/2001 |
| EP | 1 082 953 | 3/2001 |
| EP | 1 108 415 | 6/2001 |
| EP | 1 201 222 | 5/2002 |
| FR | 2 792 190 | 10/2000 |
| FR | 2 794 970 | 12/2000 |
| FR | 2 801 501 | 6/2001 |
| JP | H04-210613 | 7/1992 |
| JP | H06-9341 | 1/1994 |
| JP | H07-291826 | 11/1995 |
| JP | H07-304639 | 11/1995 |
| JP | H09-2920 | 1/1997 |
| JP | H09-110631 | 4/1997 |
| JP | H09-202714 | 8/1997 |
| JP | H10-175845 | 6/1998 |
| JP | H11-255619 | 9/1999 |
| JP | 2000-191444 | 7/2000 |
| JP | 2001-31526 | 2/2001 |
| JP | 2001-192559 | 7/2001 |
| WO | WO 98/23251 | 6/1998 |

OTHER PUBLICATIONS

Kirk-Othmer, "Encyclopedia of Chemical Technology," Third Edition, vol. 22, John Wiley & Sons, 1983, pp. 333-433.

(Continued)

*Primary Examiner*—Jyothsna Venkat
(74) *Attorney, Agent, or Firm*—Finnegan, Henderson, Farabow, Garrett, & Dunner, L.L.P.

(57) ABSTRACT

A composition for coating a keratinous fiber comprising, in a cosmetically acceptable medium, at least one volatile solvent and a nonvolatile fraction comprising:
  at least one polymer capable of adhering to a keratinous material;
  particles which are solid at 25° C. comprising at least one first material chosen from crystalline and semicrystalline materials which are solid at 25° C. and have at least one of a first order phase transition, a melting transition and a combustion transition, greater than 100° C.;
wherein the first solid particles are present in the composition in an amount such that the volume fraction of the solid particles is greater than or equal to 50% of the total volume of the nonvolatile fraction of the composition.

The composition makes it possible to obtain good curling of keratinous fibers, such as eyelashes.

84 Claims, No Drawings

OTHER PUBLICATIONS

English language Derwent Abstract of EP 0 847 752, Jun. 17, 1998.
English language Derwent Abstract of EP 0 923 928, Jun. 23, 1999.
English language Derwent Abstract of EP 1 048 282, Nov. 2, 2000.
English language Derwent Abstract of EP 1 082 953, Mar. 14, 2001.
English language Derwent Abstract of FR 2 794 970, Dec. 22, 2000.
Office Action in co-pending U.S. Appl. No. 10/195,428, dated Dec. 2, 2003.
Office Action in co-pending U.S. Appl. No. 10/195,428, dated Jun. 25, 2004.
Office Action in co-pending U.S. Appl. No. 10/195,428, dated Apr. 20, 2005.
Office Action in co-pending U.S. Appl. No. 10/195,432, dated Dec. 2, 2003.
Office Action in co-pending U.S. Appl. No. 10/195,432, dated Jun. 10, 2004.
Office Action in co-pending U.S. Appl. No. 10/195,432, dated Dec. 16, 2005.
Office Action in co-pending U.S. Appl. No. 10/195,419, dated Dec. 3, 2003.
Office Action in co-pending U.S. Appl. No. 10/195,419, dated Jun. 3, 2004.
Office Action in co-pending U.S. Appl. No. 10/195,419, dated Mar. 25, 2005.
French Search Report for FR 01 09502 dated Apr. 22, 2002 (French Priority Application for U.S. Appl. No. 10/195,430, the present application).
French Search Reportfor FR 01 09505 dated May 27, 2002 (French Priority Application for U.S. Appl. No. 10/195,419).
French Search Reportfor FR 01 09503 dated Apr. 23, 2002 (French Priority Application for U.S. Appl. No. 10/195,428).
French Search Reportfor FR 01 09504 dated May 27, 2002 (French Priority Application for U.S. Appl. No. 10/195,432).
English language Derwent Abstract for EP 1 064 924.
English language Derwent Abstract for FR 2 792 190.
Notice of Allowance in co-pending U.S. Appl. No. 10/195,419, dated Nov. 14, 2005.
Notice of Allowance in co-pending U.S. Appl. No. 10/195,428, dated Jul. 11, 2006.
English language JPO Abstract for JP-H09-2920.
English language JPO Abstract for JP-H10-175845.
English language Derwent Abstract for JP-H09-202714.
English language Derwent Abstract for JP-2001-31526.
Stedman's Medical Dictionary, 27$^{th}$ Ed. Baltimore: Lippincott, Williams and Wilkins, 2003; http://www.emedicine.com/asp/dictionary.asp?keyword=simethicone, printed on Feb. 28, 2006.

* cited by examiner

MASCARA COMPRISING SOLID PARTICLES

This application claims priority of U.S. Provisional Application No. 60/306,431, filed Jul. 20, 2001.

The subject of the present invention is a cosmetic composition for coating keratinous fibres, such as eyelashes or hair, comprising solid particles and an adherent polymer, and its use for curling keratinous fibres. The composition can be used on substantially longitudinal keratinous fibres of humans such as eyelashes or hair or alternatively false eyelashes or postiches such as wigs. For instance, the composition can be used for coating the eyelashes.

The composition may be a make-up composition, also called mascara, a composition to be applied over a make up, also called top coat, or alternatively a composition for treating keratinous fibres, such as eyelashes. For instance, the composition can be a mascara.

The aim of the present invention is to provide a composition for coating eyelashes leading, after application, to a coat conferring good curling of the eyelashes.

The inventors have discovered that such a coating of the eyelashes could be obtained using particular solid particles combined with an adherent polymer.

More precisely, the subject of the invention is a composition for coating keratinous fibres, such as eyelashes, comprising, in a cosmetically acceptable medium comprising at least one volatile solvent, a nonvolatile fraction comprising:

at least one polymer capable of adhering to the keratinous material, first particles which are solid at 25° C. comprising at least one first material chosen from crystalline and semicrystalline materials which are solid at 25° C. and have at least one of a first order phase transition, a melting transition and a combustion transition, greater than 100° C., and optionally second particles which are solid at 25° C., comprising a second material different from the first material, the second solid particles not being capable of coalescing at a temperature of less than or equal to 40° C., the first solid particles and, where appropriate, the second solid particles being present in the composition in an amount such that the volume fraction of the first solid particles and, where appropriate, of the second solid particles is greater than or equal to 50% of the total volume of the nonvolatile fraction of the composition, and, where appropriate, the volume fraction of the first solid particles being greater than or equal to 10% of the total volume fraction of the first and second solid particles.

The subject of the invention is also a method for applying make-up to or the nontherapeutic treatment of keratinous fibres, such as eyelashes, comprising the application to keratinous fibres of a composition as defined above.

The subject of the invention is also the use of a composition as defined above for curling keratinous fibres, such as eyelashes.

The subject of the invention is also the use of first solid particles comprising at least one first material chosen from crystalline and semicrystalline materials which are solid at 25° C. and have at least one of a first order phase transition, a melting transition and a combustion transition, greater than 100° C., and optionally of second solid particles comprising a second material different from the first material, the second solid particles not being capable of coalescing at a temperature of less than or equal to 40° C., in a composition for coating keratinous fibres, such as a mascara, comprising, in a cosmetically acceptable medium comprising at least one volatile solvent, a nonvolatile fraction comprising at least one polymer capable of adhering to the keratinous materials and comprising the said first and second solid particles, the first solid particles and, where appropriate, the second solid particles being present in the composition in an amount such that the volume fraction of the first solid particles and, where appropriate, of the second solid particles is greater than or equal to 50% of the total volume of the nonvolatile fraction of the composition, and, where appropriate, the volume fraction of the first solid particles being greater than or equal to 10% of the total volume fraction of the first and second solid particles, for curling keratinous fibres, such as eyelashes. The expression solid particles is defined herein to mean particles which are in the solid state at 25° C. and at atmospheric pressure.

The expression nonvolatile fraction of the composition is defined herein to mean the combination of the constituents present in the composition which are not volatile. The expression volatile compound is defined herein to mean a compound which, taken in isolation, has a non-zero vapour pressure, at room temperature (25° C.) and atmospheric pressure, such as ranging from $10^{-2}$ to 300 mmHg (1.33 Pa to 40 000 Pa), and further such as greater than 0.3 mmHg (40 Pa).

The nonvolatile fraction of the composition in fact corresponds to the mixture of the constituents remaining on the eyelashes after drying of the mascara applied to the eyelashes.

To obtain good curling of the eyelashes, the composition according to the invention comprises solid particles, called first particles, comprising. such as formed from, at least one first material which is chosen from crystalline and semicrystalline materials which are solid at room temperature (25° C.) and having at least one of a first order phase transition, a melting transition (passage from the solid state to the liquid state), and a combustion transition (passage from the solid state to the gaseous state), greater than 100° C., for instance greater than 120° C., and further for instance greater than 150° C.

The melting or combustion temperature of the first material may be measured according to the ASTM E794-98 standard.

The expression "semicrystalline material" is defined herein to mean within the context of the invention, a material, such as a polymer, comprising a crystallizable part and an amorphous part exhibiting a reversible first order phase transition temperature, for example a melting point (solid-liquid transition).

In an embodiment of the invention, the first material of the said particles exhibits a Vickers hardness greater than or equal to 10, for example ranging from 10 to 7500, such as greater than or equal to 200, further for example ranging from 200 to 7500, and further such as greater than or equal to 400, such as, for example, ranging from 400 to 7500.

The VICKERS hardness (HV) is determined by applying to the material a penetrometer in the form of a square-base pyramid, using a load P. The mean size of a diagonal of the square impression obtained with the penetrometer is then measured.

The VICKERS hardness (HV) is then calculated by the relationship:

$$HV = \frac{1854.4 \times P}{d^2} \quad \begin{array}{l} d = \text{mean diagonal in } \mu m \\ P = \text{load applied in g} \end{array}$$

The measurement of the VICKERS hardness may be carried out using the microdurometer M 400 g 2 from the company LECO.

The first material of the said first particles may be an inorganic material which may be chosen from silica, glass, diamond, copper, boron nitride, ceramics, metal oxides, such as iron oxides, such as black iron oxide, red iron oxide, and yellow iron oxide, titanium oxides, micas, alumina and polymers such as polyamides, for example nylon, and mixtures thereof.

The said first particles may be solid particles, or alternatively hollow particles. For example, there may be used the hollow silica sold under the name "SUNSIL-130" by the company SUNJIN CHEMICAL.

According to an embodiment of the composition according to the invention, the said first particles are essentially formed of the said first material defined above.

According to another embodiment of the composition according to the invention, the said first solid particles comprise, or are even formed essentially of, at least two different first materials. This is, for example, the case of micas coated with titanium oxide or with iron oxide.

According to yet another embodiment of the composition according to the invention, the said first solid particles comprise at least the said first material, and at least an additional material, different from the said first material, said first material forming the surface of the said first particles. For these solid particles, the said first material having the characteristics described above, exists at the surface of the said first particles, the latter comprising an additional material coated with the first material.

In an embodiment of the invention, the said first solid particles may have, for example, a mean size ranging from 5 nm to 50 μm, for instance from 20 nm to 50 μm as measured by methods known to those skilled in the art.

The composition according to the invention may comprise, in addition to the first solid particles described above, other solid particles, called second solid particles, different from the first solid particles.

These second particles correspond to the particles which are solid at 25° C. of any material, different from the first particles, remaining in the form of individualized particles, or optionally of particles stuck together but which retain, in this case, their individual particle state (these particles stuck together are not coalesced at a temperature of less than or equal to 40° C.).

For instance, the second solid particles may be chosen from:
 particles which are solid at 25° C., called second primary solid particles, comprising, such as formed of, at least one amorphous material having a glass transition temperature of greater than or equal to 60° C.,
 other particles which are solid at 25° C., called second tertiary solid particles, different from the said second primary particles
 and mixtures thereof.

The second primary solid particles comprise, such as formed of, at least one amorphous material, such as a polymer, having a glass transition temperature greater than or equal to 60° C. (for instance ranging from 60° C. to 800° C.), such as greater than or equal to 80° C. (for instance ranging from 80° C. to 700° C.), further such as greater than or equal to 100° C. (even further for instance ranging from 100° C. to 500° C.). The glass transition temperature may be measured by DSC (Differential Scanning Calorimetry) according to the ASTM D3418-97 standard.

As amorphous material, there may be used a polymer which is nonfilm-forming at a temperature of less than or equal to 40° C. which has a glass transition temperature as described above.

The expression "nonfilm-forming polymer at a temperature of less than or equal to 40° C." is defined herein to mean a polymer which is not capable of forming, on its own or in the presence of a film-forming aid, a continuous film which is adherent to a support, such as to a keratinous material, at a temperature of less than or equal to 40° C.

The expression film-forming aid is defined herein to mean plasticizing agents and coalescing agents known to persons skilled in the art for promoting film formation by polymers.

As representative amorphous polymer having a glass transition temperature of greater than or equal to 60° C., there may be used free-radical polymers or polycondensates having the defined glass transition temperature.

As free-radical polymer, there may be mentioned:
 polymers of ethylene, such as of cycloethylene, and of naphthylethylene;
 polymers of propylene, such as of hexafluoropropylene;
 acrylic polymers, such as polymers of acrylic acid, of dimethyl-adamanthyl acrylate, of chloroacrylate;
 polymers of acrylamide;
 polymers of (meth)acrylonitrile;
 polymers of acetylstyrene, of carboxystyrene, of chloromethylstyrene.

As polycondensates, there may be mentioned polycarbonates, polyurethanes, polyesters, polyamides, polysulphones, polysulphonamides and carbohydrates such as amylose triacetate.

The second primary solid particles may be solid particles or hollow particles.

According to one embodiment, the second primary solid particles are essentially formed of the said amorphous material described above.

According to another embodiment, the second primary solid particles comprise at least the said amorphous material and at least one additional material, different from the amorphous material, the said amorphous material forming the surface, or the crust, of the said second primary solid particles and the additional material forming the inside, or the core, of the said second primary solid particles.

The additional material may be, for example, an additional polymer having a glass transition temperature of less than 60° C., for instance less than 45° C.

Thus, the second primary solid particles may be, for example, core-shell particles of polymers comprising an outer part (that is to say a crust) formed of the first amorphous material having a glass transition temperature of greater than or equal to 60° C. and comprising an inner part (that is to say a core) having a glass transition temperature of less than 60° C.

For example, the content of the amorphous material in the second primary solid particles is such that the volume fraction of the amorphous material is greater than or equal to 10%, such as greater than or equal to 30%, by volume of the total volume of the second primary solid particles.

The second primary solid particles may have a mean size ranging from 10 nm to 50 µm, for instance ranging from 20 nm to 1 µm, as measured by methods known to those skilled in the art.

As second primary solid particles, there may be used aqueous dispersions of nonfilm-forming polymer which are sold under the names "JONCRYL® SCX 8082", "JONCRYL® 90" by the company JOHNSON POLYMER, "NEOCRYL® XK 52" by the company AVECIA RESINS and "RHODOPAS® 5051" by the company RHODIA CHIMIE.

All the constituents present in the composition according to the invention existing in the state of solid particles at 25° C. and which do not coalesce at a temperature of less than or equal to 40° C., on their own or in the presence of the other constituents present in the composition, are considered as being either first solid particles or second solid particles according to the definitions described above.

Second secondary particles may, for example, be made of a material chosen from waxes, fillers, polymers different from the amorphous material present in the second primary solid particles described above.

The additives described below, when they are in the form of solid particles at 25° C., are considered as being either first solid particles or second solid particles as described above when these additives possess the corresponding characteristics defined above.

In an embodiment of the invention, the adherent polymer present in the composition according to the invention may be in the form of solid particles. In this case, these particles are considered as being solid particles as defined above if this polymer possesses the characteristics defined above.

In the composition according to the invention, the said first and, where appropriate, the second solid particles are present in an amount such that the volume fraction of the first solid particles and, where appropriate, of the second solid particles is greater than or equal to 50% of the total volume of the nonvolatile fraction of the composition, which means that the total volume of all the first particles and, where appropriate, of the second particles represents at least 50% (such as ranging from 50% to 99%) of the total volume of the nonvolatile fraction of the composition.

The expression "volume fraction of the first solid particles and, where appropriate, of the second solid particles" is defined herein to mean the percentage total volume of all the first solid particles and, where appropriate, of all the second solid particles present in the nonvolatile fraction of the composition, relative to the total volume of all the compounds of the nonvolatile fraction of the composition.

For example, the said volume fraction of the first solid particles and, where appropriate, of the second solid particles is greater than or equal to 60% (such as ranging from 60% to 99%), or greater than or equal to 70% (such as ranging from 70% to 95%) of the total volume of the nonvolatile fraction of the composition.

The volume fraction (VF) of solid particles present in the nonvolatile fraction of the composition is defined herein as the percentage total volume V of the said particles divided by the total volume V' of the nonvolatile fraction of the composition.

The volume V of solid particles is equal to the mass m of the said solid particles in the composition divided by the density d of the particles. The density is calculated according to the method described below.

Volume fraction: $VF=100 \times V/V'$ and $V=m/d$

The total volume V' of the nonvolatile fraction of the composition is calculated by adding the volume of each nonvolatile constituent present in the composition.

For example, when the composition comprises second particles as defined above, the first particles are present in the composition in an amount such that the volume fraction of the first solid particles is greater than or equal to 10% of the total volume fraction of the first and second solid particles, such as ranging from 10% to 100%, further such as greater than or equal to 20%, even further such as ranging from 20% to 100%, still further greater than or equal to 30%, even still further ranging from 30% to 100%, further still greater than or equal to 40%, such as ranging from 40% to 100%, and even further still greater than or equal to 50%, such as ranging from 50% to 100%.

For instance, when the composition comprises second primary solid particles as described above, the volume fraction of the said first solid particles and of the said second primary solid particles is greater than or equal to 10.05% (such as ranging from 10.05% to 100%) of the total volume of the first and second solid particles, such as greater than or equal to 20.05% (such as ranging from 20.05% to 100%), further such as greater than or equal to 30.05% (such as ranging from 30.05% to 100%), further still greater than or equal to 40.05% (such as ranging from 40.05% to 100%), and even further still greater than or equal to 50% (such as ranging from 50% to 100%).

The volatile solvent present in the composition according to the invention may be chosen from water, the volatile organic solvents defined below, the volatile oils defined below, and mixtures thereof.

In the present application, the expression "polymer capable of adhering to the keratinous materials", called later adherent polymer, is defined herein to mean a polymer capable of resting attached to a keratinous material like keratinous fibres such as the eyelashes, the hair or the skin, during contact of the polymer with the said keratinous materials. Such an adherent polymer in fact has a good capacity to form a deposit on a keratinous material and remains attached to the latter for a normal period of wear.

For example, the adherent polymer may be a film-forming polymer at a temperature of less than or equal to 40° C. In the present application, the expression "film-forming polymer" is defined herein to mean a polymer capable of forming, on its own or in the presence of a film-forming aid, a continuous deposit, such as a film, which adheres to a support, such as to a keratinous material.

The adherent polymer present in the composition according to the invention may be a polymer solubilized or dispersed in the form of solid particles in an aqueous phase of the composition or alternatively solubilized or dispersed in the form of solid particles in a liquid fatty phase. The composition may comprise a mixture of these polymers. When the adherent polymer exists in the form of solid particles, these particles may have a mean particle size ranging from 5 nm to 10 µm, such as ranging from 5 nm to 5 µm, further such as ranging from 5 nm to 600 nm, and further such as ranging from 20 nm to 300 nm, as measured by methods known to those skilled in the art.

The adherent polymer may be present in the composition according to the invention in a dry matter content ranging from 0.1% to 50% by weight relative to the total weight of the composition, such as from 0.5% to 40% by weight, and further such as from 1% to 30% by weight.

Among the adherent polymers which can be used in the composition of the present invention, there may be mentioned synthetic polymers of the free-radical type or of the polycondensate type, polymers of natural origin and mixtures thereof.

The expression free-radical polymer is defined herein to mean a polymer obtained by polymerization of monomers with ethylenic unsaturation, for example, each monomer being capable of homopolymerizing (in contrast to polycondensates).

The polymers of the free-radical type may be vinyl polymers or copolymers, or acrylic polymers, for example.

The vinyl polymers may result from the polymerization of ethylenically unsaturated monomers having at least one acid group and/or esters of these acid monomers and/or amides of these acid monomers.

As a monomer carrying an acid group, there may be used $\alpha,\beta$-ethylenic unsaturated carboxylic acids such as acrylic acid, methacrylic acid, crotonic acid, maleic acid, or itaconic acid.

The esters of acid monomers can be chosen from the esters of (meth)acrylic acid (also called (meth)acrylates), for example alkyl, such as $C_1$–$C_{30}$, further such as $C_1$–$C_{20}$, alkyl, (meth)acrylates, aryl, such as $C_6$–$C_{10}$ aryl, (meth) acrylates, hydroxyalkyl, such as $C_2$–$C_6$ hydroxyalkyl, (meth)acrylates.

Among the alkyl (meth)acrylates, there may be mentioned methyl methacrylate, ethyl methacrylate, butyl methacrylate, isobutyl methacrylate, 2-ethylhexyl methacrylate, lauryl methacrylate, and cyclohexyl methacrylate.

Among the hydroxyalkyl (meth)acrylates, there may be mentioned hydroxyethyl acrylate, 2-hydroxypropyl acrylate, hydroxyethyl methacrylate, and 2-hydroxypropyl methacrylate.

Among the aryl (meth)acrylates, there may be mentioned benzyl acrylate and phenyl acrylate.

The esters of (meth)acrylic acid which can be chosen are the alkyl (meth)acrylates.

According to an embodiment of the present invention, the alkyl group of the esters may be either fluorinated or perfluorinated, that is to say that some or all of the hydrogen atoms of the alkyl group are substituted with fluorine atoms.

As amides of the acid monomers, there may be mentioned for example (meth)acrylamides, and N-alkyl(meth)acrylamides, such as of a $C_2$–$C_{12}$ alkyl. Among the N-alkyl(meth) acrylamides, there may be mentioned N-ethylacrylamide, N-t-butylacrylamide, N-t-octylacrylamide, and N-undecylacrylamide.

The vinyl polymers may also result from the homopolymerization or copolymerization of monomers chosen from vinyl esters and styrene monomers. For example, these monomers may be polymerized with acid monomers and/or their esters and/or their amides, such as those mentioned above.

As examples of vinyl esters, there may be mentioned vinyl acetate, vinyl neodecanoate, vinyl pivalate, vinylbenzoate, and vinyl t-butyl benzoate.

As styrene monomers, there may be mentioned styrene and alpha-methylstyrene.

It is possible to use any monomer known to a person skilled in the art entering into the categories of acrylic and vinyl monomers (including the monomers modified by a silicone chain).

Among the polycondensates, there may be mentioned polyurethanes, polyesters, polyester amides, polyamides, epoxy ester resins, and polyureas.

The polyurethanes may be chosen from anionic, cationic, nonionic, or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The polyesters may be obtained, in a known manner, by polycondensation of dicarboxylic acids with polyols, such as diols.

The dicarboxylic acid may be aliphatic, alicyclic, or aromatic. There may be mentioned as examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecane-dioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid, and 2,6-naphthalenedicarboxylic acid. These dicarboxylic acid monomers may be used alone or in combination with at least two dicarboxylic acid monomers. Among these monomers, phthalic acid, isophthalic acid and terephthalic acid may, for example, be chosen.

The diol maybe chosen from aliphatic, alicyclic, or aromatic diols, such as ethylene glycol, diethylene glycol, triethylene glycol, 1,3-propanediol, cyclohexanedimethanol and 4-butanediol. As other exemplary polyols, there may be mentioned glycerol, pentaerythritol, sorbitol, trimethylolpropane.

The polyester amides may be obtained in a manner similar to the polyesters, by polycondensation of diacids with diamines or amino alcohols. As diamine, there may be used ethylenediamine, hexamethylenediamine, meta- or para-phenylenediamine. As aminoalcohol, monoethanolamine may be used.

The polyester may, in addition, comprise at least one monomer carrying at least one —$SO_3M$ group, with M representing a hydrogen atom, an ammonium ion $NH_4^+$, or an alkali, alkaline-earth, or metal ion, such as for example an $Na^+$, $Li^+$, $K^+$, $Mg^{2+}$, $Ca^{2+}$, $Cu^{2+}$, $Fe^{2+}$, or $Fe^{3+}$ ion. There may also be used a bifunctional aromatic monomer comprising such an —$SO_3M$ group.

The aromatic ring of the bifunctional aromatic monomer carrying, in addition, an —$SO_3M$ group as described above may be chosen for example from benzene, naphthalene, anthracene, diphenyl, oxydiphenyl, sulphonyldiphenyl, and methylenediphenyl rings. There may also be mentioned as examples of a bifunctional aromatic monomer carrying, in addition, an —$SO_3M$ group: sulphoisophthalic acid, sulphoterephthalic acid, sulphophthalic acid, 4-sulphonaphthalene-2,7-dicarboxylic acid.

Copolymers based on isophthalate/sulphoisophthalate; copolymers obtained by condensation of diethylene glycol, cyclohexanedimethanol, isophthalic acid, and sulphoisophthalic acid can also be used. Such polymers are sold, for example, under the trade name Eastman AQ® by the company Eastman Chemical Products.

The optionally modified polymers of natural origin may be chosen from shellac resin, sandarac gum, dammars, elemis, copals, cellulosic polymers, and mixtures thereof.

According to an embodiment of the composition according to the invention, the adherent polymer may be present in the form of solid particles in aqueous dispersion, generally known as latex or pseudolatex. The techniques for preparing these dispersions are well known to persons skilled in the art.

As an aqueous dispersion of adherent polymer, there may, for example, be used the acrylic dispersions sold under the names NEOCRYL XK-90®, NEOCRYL A-1070®, NEOCRYL A-1090®, NEOCRYL BT-62®, NEOCRYL A-1079®, NEOCRYL A-523® by the company AVECIA-NEORESINS, DOW LATEX 432® by the company DOW CHEMICAL, DAITOSOL 5000 AD® by the company DAITO KASEY KOGYO; as well as the aqueous dispersions of polyurethane which are sold under the names NEOREZ R-981®, NEOREZ R-974® by the company AVECIA-NEORESINS, AVALURE UR-405®, AVALURE UR-410®, AVALURE UR-425®, AVALURE UR-450®, SANCURE 875®, SANCURE 861®, SANCURE 878®, SANCURE 2060® by the company GOODRICH, IMPRANIL 85® by the company BAYER, and AQUAMERE H-1511® by the company HYDROMER.

As an aqueous dispersion of adherent polymer, there may also be used the dispersions of polymers resulting from the free-radical polymerization of one or more free-radical monomers inside and/or partly at the surface, of preexisting particles of at least one polymer chosen from polyurethanes, polyureas, polyesters, polyesteramides, and/or alkyds. These polymers are generally called hybrid polymers.

According to another embodiment of the composition according to the invention, the at least one adherent polymer may be a water-soluble polymer and is therefore present in the aqueous phase of the composition in solubilized form. As examples of film-forming, water-soluble polymers, there may be mentioned proteins such as proteins of plant origin, such as wheat or soya bean proteins; proteins of animal origin such as keratin, for example keratin hydrolysates and sulphonic keratins;

anionic, cationic, amphoteric, or nonionic polymers of chitin or chitosan;

cellulose polymers such as hydroxyethyl cellulose, hydroxypropyl cellulose, methyl cellulose, ethyl hydroxyethyl cellulose, carboxymethyl cellulose, and quaternized derivatives of cellulose;

acrylic polymers or copolymers such as polyacrylates or polymethacrylates;

vinyl polymers, such as polyvinylpyrrolidones, copolymers of methyl vinyl ether and maleic anhydride, the copolymer of vinyl acetate and crotonic acid, copolymers of vinylpyrrolidone and vinyl acetate; copolymers of vinylpyrrolidone and caprolactam; polyvinyl alcohol;

optionally modified polymers of natural origin, such as:
  gum arabic, guar gum, xanthan derivatives, karaya gum;
  alginates and carrageenans;
  glycoaminoglycans, hyaluronic acid and its derivatives;
  shellac resin, sandarac gum, dammars, elemis, copals;
  deoxyribonucleic acid;
  muccopolysaccharides such as hyaluronic acid, chondroitin sulphates, and mixtures thereof.

According to another embodiment of the composition according to the invention, the at least one adherent polymer may be present in a liquid fatty phase dispersed in the aqueous phase (aqueous medium) of the composition, the liquid fatty phase comprising oils or organic solvents such as those described above. The expression "liquid fatty phase" is defined herein to mean, in the context of the invention, a fatty phase which is liquid at room temperature (25° C.) and atmospheric pressure (760 mmHg, that is $10^5$ Pa), composed of one or more fatty substances which are liquid at room temperature, also called oils, which are generally compatible with each other.

For example, the liquid fatty phase comprises a volatile oil, optionally in the form of a mixture with a nonvolatile oil, it being possible for the oils to be chosen from the oils cited below.

According to yet another embodiment of the composition according to the invention, the at least one adherent polymer may be present in the form of surface-stabilized particles dispersed in the liquid fatty phase.

The dispersion of surface-stabilized polymer particles may be manufactured as described in the document EP-A-749747, the disclosure of which is incorporated herein by reference.

The polymer particles are surface-stabilized using a stabilizer which may be a block polymer, a graft polymer and/or a random polymer, alone or in the form of a mixture.

Dispersions of film-forming polymer in the liquid fatty phase, in the presence of stabilizing agents, are described in the documents EP-A-749746, EP-A-923928, EP-A-930060, the disclosures of which are incorporated herein by reference.

The size of the polymer particles in dispersion either in the aqueous phase or in the liquid fatty phase may range from 5 nm to 10 µm, such as from 5 nm to 5 µm, further such as ranging from 5 nm to 600 nm, and even further such as from 20 nm to 300 nm, as measured by methods known to those skilled in the art.

According to yet another embodiment of the composition according to the invention, the adherent polymer may be solubilized in the liquid fatty phase; the film-forming polymer is then said to be a fat-soluble polymer.

By way of example of a fat-soluble polymer, there may be mentioned copolymers of vinyl ester (the vinyl group being directly linked to the oxygen atom of the ester group and the vinyl ester having a linear or branched saturated hydrocarbon radical of 1 to 19 carbon atoms, linked to the carbonyl of the ester group) and of at least one other monomer which may be chosen from vinyl esters (different from the vinyl ester already present), α-olefins (having from 8 to 28 carbon atoms), alkyl vinyl ethers (in which the alkyl group comprises from 2 to 18 carbon atoms), and allyl and methallyl esters (having a linear or branched saturated hydrocarbon radical of 1 to 19 carbon atoms, linked to the carbonyl of the ester group).

These copolymers may be crosslinked using crosslinking agents which may be either of the vinyl type, or of the allyl or methallyl type, such as tetraallyloxyethane, divinylbenzene, divinyl octanedioate, divinyl dodecanedioate, and divinyl octadecanedioate.

As examples of these copolymers, there may be mentioned the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate, crosslinked with 0.2% of divinylbenzene, vinyl dimethyl propionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene and allyl propionate/allyl stearate crosslinked with 0.2% of divinylbenzene.

As fat-soluble polymers, there may also be mentioned fat-soluble homopolymers, such as those resulting from the homopolymerization of vinyl esters having from 9 to 22 carbon atoms or of alkyl acrylates or methacrylates, the alkyl radicals having from 10 to 20 carbon atoms.

Such fat-soluble homopolymers may be chosen from polyvinyl stearate, polyvinyl stearate crosslinked using divinylbenzene, diallyl ether or diallyl phthalate, polystearyl (meth)acrylate, polyvinyl laurate, polylauryl (meth)acrylate, it being possible for these poly(meth)acrylates to be crosslinked using ethylene glycol or tetraethylene glycol dimethacrylate.

The fat-soluble copolymers and homopolymers defined above are known and described in application FR-A-2232303, the disclosure of which is incorporated herein by reference; they may have a weight-average molecular weight ranging from 2,000 to 500,000, such as from 4,000 to 200,000.

As film-forming, fat-soluble polymers which can be used in the invention, there may also be mentioned polyalkylenes, such as copolymers of $C_2-C_{20}$ alkenes, such as polybutene, alkyl celluloses with a saturated or unsaturated, linear or branched, $C_1$ to $C_8$ alkyl radical such as ethyl cellulose and propyl cellulose, copolymers of vinylpyrrolidone (VP) and copolymers of vinylpyrrolidone and of a $C_2$ to $C_{40}$ alkene, such as a $C_3$ to $C_{20}$ alkene. By way of example of a VP copolymer which can be used in the invention, there may be mentioned the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene, and VP/acrylic acid/lauryl methacrylate copolymer.

The composition according to the invention may comprise a film-forming aid which promotes the formation of a film with the film-forming polymer. Such a film-forming agent may be chosen from all the compounds known to persons skilled in the art to be capable of fulfilling the desired function, and may be chosen from plasticizing agents and coalescing agents.

According to an embodiment of the composition according to the invention, the at least one adherent polymer may be chosen from polymers capable of forming a deposit, such as a film, producing, at a concentration of 7% in water, a retraction of isolated stratum corneum of more than 1% at 30° C. under a relative humidity of 40%, for example of more than 1.2%, and for further example of more than 1.5%. This retraction is measured using an extensiometer, according to the method described below.

The volatile solvent present in the composition may be chosen from water or volatile organic compounds, or mixtures thereof.

According to one embodiment of the composition according to the invention, the composition may comprise an aqueous medium, constituting an aqueous phase, which may be the continuous phase of the composition.

The aqueous phase may comprise, or may essentially comprise, water; it may also comprise a mixture of water and a water-miscible organic solvent (solvent capable of forming with water a homogeneous mixture transparent to the eye at 25° C.) such as lower monoalcohols having from 1 to 5 carbon atoms such as ethanol, isopropanol, glycols having from 2 to 8 carbon atoms such as propylene glycol, ethylene glycol, 1,3-butylene glycol, dipropylene glycol, $C_3-C_4$ ketones, and $C_2-C_4$ aldehydes.

The aqueous phase (water and optionally the water-miscible organic solvent) may, for example, be present in an amount ranging from 0.1% to 98% by weight, relative to the total weight of the composition, such as from 1% to 80% by weight, and further such as from 5% to 65% by weight.

According to another embodiment of the composition according to the invention, the composition may comprise at least one volatile organic solvent or oil which may form a fatty phase, such as a continuous fatty phase. The composition may be an anhydrous composition.

The expression "volatile organic solvent or volatile oil" is defined herein to mean, in the context of the invention, volatile cosmetic oils and organic solvents, which are liquid at room temperature, having a non-zero vapour pressure, at room temperature and atmospheric pressure, ranging, for example, from $10^{-2}$ to 300 mmHg (1.33 Pa to 40 000 Pa) such as greater than 0.3 mmHg (40 Pa). The expression "nonvolatile oil" is defined herein to mean an oil having a vapour pressure of less than $10^{-2}$ mmHg (1.33 Pa) at room temperature and atmospheric pressure.

These oils may be hydrocarbon oils, silicone oils, fluorinated oils, and mixtures thereof.

The expression "hydrocarbon oil" is defined herein to mean an oil comprising mainly hydrogen and carbon atoms and optionally oxygen, nitrogen, sulphur, and phosphorus atoms. The volatile hydrocarbon oils may be chosen from hydrocarbon oils having from 8 to 16 carbon atoms, for instance branched $C_8-C_{16}$ alkanes such as $C_8-C_{16}$ isoalkanes of petroleum origin (also called isoparaffins) such as isododecane (also called 2,2,4,4,6-pentamethylheptane), isodecane, isohexadecane, and for example the oils sold under the trade names Isopars' or Permetyls, $C_8-C_{16}$ branched esters, isohexyl neopentanoate, and mixtures thereof. Other volatile hydrocarbon oils such as petroleum distillates, such as those sold under the name Shell Solt by the company SHELL, may also be used. For example, the volatile solvent can be chosen from volatile hydrocarbon oils having from 8 to 16 carbon atoms and mixtures thereof.

As volatile oils, there may also be used volatile silicones, such as for example volatile linear or cyclic silicone oils, such as those having a viscosity $\leq 8$ centistokes ($8 \times 10^{-6}$ m$^2$/s), and having, for example, from 2 to 7 silicon atoms, these silicones optionally comprising alkyl or alkoxy groups having from 1 to 10 carbon atoms. As volatile silicone oil which can be used in the invention, there may be mentioned octamethylcyclotetrasiloxane, decamethylcyclopentasiloxane, dodecamethylcyclohexasiloxane, heptamethylhexyltrisiloxane, heptamethyl-octyltrisiloxane, hexamethyldisiloxane, octamethyltri-siloxane, decamethyltetrasiloxane, dodecamethylpenta-siloxane, and mixtures thereof.

As volatile fluorinated solvent, perfluoromethylcyclopentane or 1,1,1,2,2,3,4,5,5,5-decafluoropentane may be used.

The volatile oil may be present in the composition according to the invention in an amount ranging from 0.1% to 98% by weight, relative to the total weight of the composition, such as ranging from 1% to 65% by weight, and further such as ranging from 5% to 65% by weight.

The composition may also comprise at least one nonvolatile oil in particular chosen from nonvolatile hydrocarbon oils, silicone oils, and fluorinated oils.

As nonvolatile hydrocarbon oil, there may be mentioned.
  hydrocarbon oils of plant origin such as triglycerides comprising esters of fatty acids and of glycerol in which the fatty acids may have varying chain lengths from $C_4$ to $C_{24}$, it being possible for the latter to be linear or branched, saturated or unsaturated; these oils can be, for example, wheatgerm oil, sunflower oil, grapeseed oil, sesame oil, maize oil, apricot oil, castor oil, karite oil, avocado oil, olive oil, soyabean oil, sweet almond oil, palm oil, rapeseed oil, cottonseed oil, hazelnut oil, macadamia oil, jojoba oil, lucerne oil, poppyseed oil, pumpkinseed oil, sesame oil, gourd oil, rapeseed oil, blackcurrant seed oil, evening primrose oil, millet oil, barley oil, quinoa oil, rye oil, safflower oil, candlenut oil, passionflower oil, rose-muscat oil; as well as triglycerides of caprylic/capric acids such as those sold by the company Stéarineries Dubois or those sold under the names Miglyol 810, 812 and 818 by the company Dynamit Nobel, synthetic ethers comprising from 10 to 40 carbon atoms;

linear or branched hydrocarbons of mineral or synthetic origin such as petroleum jelly, polydecenes, hydrogenated polyisobutene such as parleam, squalane, and mixtures thereof;

synthetic esters such as the oils of formula $R_1COOR_2$ in which $R_1$ represents the residue of a linear or branched fatty acid comprising from 1 to 40 carbon atoms and $R_2$ represents a hydrocarbon chain, such as a branched hydrocarbon chain, comprising from 1 to 40 carbon atoms provided that $R_1+R_2$ is $\geq 10$, such as for example Purcellin oil (ketostearyl octanoate), isopropyl myristate, isopropyl palmitate, $C_{12}$ to $C_{15}$ alcohol benzoate, hexyl laurate, diisopropyl adipate, isononyl isononanoate, 2-ethylhexyl palmitate, isostearyl isostearate, octanoates, decanoates or ricinoleates of alcohols or of polyalcohols such as propylene glycol dioctanoate; hydroxylated esters such as isostearyl lactate, diisostearyl malate; and esters of pentaerythritol;

fatty alcohols which are liquid at room temperature containing a branched and/or unsaturated carbon chain comprising from 12 to 26 carbon atoms such as octyl dodecanol, isostearyl alcohol, oleyl alcohol, 2-hexyldecanol, 2-butyloctanol, 2-undecylpentadecanol;

higher fatty acids such as oleic acid, linoleic acid, and linolenic acid;

dicaprylyl carbonate sold under the name "CETIOL CC" by the company COGNIS; and mixtures thereof.

The nonvolatile silicone oils which can be used in the composition according to the invention may be nonvolatile polydimethylsiloxanes (PDMS), polydimethylsiloxanes comprising alkyl or alkoxy groups, pendant and/or at the silicone chain end, the alkyl and alkoxy groups each comprising from 2 to 24 carbon atoms, phenylated silicones such as phenyltrimethicones, phenyldimethicones, phenyltrimethylsiloxydi-phenylsiloxanes, diphenyidimethicones, diphenylmethyl-diphenyltrisiloxanes, (2-phenylethyl)trimethylsioloxy-silicates.

The fluorinated oils which can be used in the invention can be fluorosilicone oils, fluorinated polyethers, and fluorinated silicones, as described in the document EP-A-847752, the disclosure of which is incorporated herein by reference.

The nonvolatile oils may, for example, be present in the composition according to the invention in an amount ranging from 0.1% to 50% by weight, such as from 0.1% to 30% by weight, relative to the total weight of the composition, and further such as from 0.1% to 20% by weight.

The composition according to the invention may also comprise at least one wax. The expression "wax" is defined herein to mean, within the context of the present invention, a lipophilic fatty compound, which is solid at room temperature (25° C.) and atmospheric pressure (760 mmHg, that is $10^5$ Pa), with a reversible solid/liquid change of state, having a melting point ranging from 30° C. to 99° C., for instance ranging from 45° C. to 99° C.

By heating the wax to its melting point, it is possible to make it miscible with oils and to form a microscopically homogeneous mixture, but on bringing the temperature of the mixture back to room temperature, recrystallization of the wax in the oils of the mixture is obtained.

The melting point values correspond, according to the invention, to the peak of melting measured using a differential scanning calorimeter (DSC), for example the calorimeter sold under the name DSC 30 by the company METLER, with a rise in temperature of 5 or 10° C. per minute.

The waxes, for the purposes of the invention, are those generally used in the cosmetic and dermatological fields. There may be mentioned beeswax, lanolin wax, and Chinese waxes; rice wax, Carnauba wax, Candelilla wax, Ouricury wax, sugarcane wax, Japan wax, and sumac wax; montan wax, microcrystalline waxes, paraffin waxes, ozokerites, ceresin wax, lignite wax, polyethylene waxes, the waxes obtained by Fischer-Tropsch synthesis, fatty acid esters, and glycerides which are concrete at 40° C., such as at over 55° C.

There may also be mentioned the waxes obtained by catalytic hydrogenation of animal or vegetable oils having linear or branched $C_8$–$C_{32}$ fatty chains. Among these, there may be mentioned hydrogenated jojoba oil, hydrogenated sunflower oil, hydrogenated castor oil, hydrogenated copra oil, and hydrogenated lanolin oil.

Silicone waxes or fluorinated waxes may also be mentioned.

The waxes present in the composition may be dispersed in the form of particles in an aqueous medium. These particles may have a mean size ranging from 50 nm to 50 μm, such as from 50 nm to 10 μm as measured by methods known to those skilled in the art.

For example, the wax may be present in the form of a wax-in-water emulsion, it being possible for the waxes to be in the form of particles having a mean size ranging from 1 μm to 50 μm, such as from 1 μm to 10 μm, as measured by methods known to those skilled in the art.

In another embodiment of the composition according to the invention, the wax may be present in the form of a wax microdispersion, the wax being in the form of particles whose mean size is less than 1 μm, and ranges from 50 nm to 500 nm, as measured by methods known to those skilled in the art. Wax microdispersions are described in the documents EP-A-557196 and EP-A-1048282, the disclosures of which are incorporated herein by reference.

The wax may be present in the composition according to the invention in an amount ranging from 0.1% to 50% by weight, relative to the total weight of the composition, such as from 0.5% to 30% by weight, and further such as from 1% to 20% by weight.

The composition according to the invention may contain at least one emulsifying surfactant present in a proportion ranging, for example, from 2 to 30% by weight relative to the total weight of the composition, such as from 5% to 15%. These surfactants may be chosen from anionic and nonanionic surfactants. Reference may be made to the document "Encyclopedia of Chemical Technology, KIRK-OTHMER", volume 22, p. 333–432, $3^{rd}$ edition, 1979, WILEY (the disclosure of which is incorporated herein by reference), for the definition of the properties and functions (emulsifier) of the surfactants, such as on p. 347–377 of this reference, for anionic and nonionic surfactants.

The surfactants which can be used in the composition according to the invention are chosen:

from nonionic surfactants: fatty acids, fatty alcohols, polyethoxylated and polyglycerolated fatty alcohols such as polyethoxylated stearyl and cetylstearyl alcohols, esters of fatty acid and of sucrose, esters of alkyl glucose, polyoxyethylenated fatty esters of $C_1$–$C_6$ alkyl glucose, and mixtures thereof;

from anionic surfactants: $C_{16}$–$C_{30}$ fatty acids neutralized with amines, aqueous ammonia or alkaline salts and mixtures thereof; oxyethylenated acrylic acid/ monostearyl itaconate copolymer (20 EO) as an aqueous dispersion at 30% by weight sold under the name "STRUCTURE 2001" by the company National Starch, ethoxylated acrylic acid/monocetyl itaconate copolymer (20 EO) as an aqueous dispersion at 30% sold under the name "STRUCTURE 3001" by the company National Starch.

Surfactants which allow the production of an oil-in-water or wax-in-water emulsion can be used.

The composition according to the invention may also comprise a colouring substance such as pulverulent colouring substances, fat-soluble colorants, water-soluble colorants. This colouring substance may be present in an amount ranging from 0.01% to 50% by weight, relative to the total weight of the composition, such as ranging from 0.01% to 30% by weight.

The pulverulent colouring substances may be chosen from pigments and pearlescent agents.

The pigments may be white or coloured, inorganic and/or organic, coated or otherwise. There may be mentioned, among the inorganic pigments, titanium dioxide, optionally surface-treated, zirconium, zinc or cerium oxides, as well as iron or chromium oxides, manganese violet, ultramarine blue, chromium hydrate and ferric blue. Among the organic pigments, there may be mentioned carbon black, pigments of the D & C type, and lacquers based on carmine, barium, strontium, calcium, and aluminium.

The pearlescent agents may be chosen from white pearlescent pigments such as mica coated with titanium or bismuth oxychloride, coloured pearlescent pigments such as mica-titanium with iron oxides, mica-titanium with ferric blue or chromium oxide, mica-titanium with an organic pigment of the abovementioned type as well as pearlescent pigments based on bismuth oxychloride.

The fat-soluble colorants are, for example, Sudan red, D&C Red 17, D&C Green 6, β-carotene, soyabean oil, Sudan brown, D&C Yellow 11, D&C Violet 2, D&C Orange 5, quinoline yellow, annatto. The water-soluble colorants are, for example, sugarbeet juice and methylene blue.

The composition of the invention may comprise, in addition, any additive conventionally used in cosmetics, such as antioxidants, fillers, preservatives, perfumes, neutralizing agents, thickeners, coalescing agents, plasticizers, cosmetic and dermatological active agents such as, for example, emollients, moisturizers, vitamins, sunscreens, and mixtures thereof. These additives may be present in the composition in an amount ranging, for example, from 0.01 to 20% of the total weight of the composition, such as from 0.01 to 10%.

The composition according to the invention may be provided in the form of an oil-in-water emulsion, a water-in-oil emulsion, a wax-in-water dispersion, or alternatively may be an anhydrous composition.

Of course persons skilled in the art will be careful to choose the possible additional additives and/or their quantity such that the advantageous properties of the composition according to the invention are not or not substantially impaired by the addition envisaged.

The composition according to the invention may be manufactured by known methods which are generally used in the cosmetic or dermatological field.

For instance, the composition according to the invention does not contain:

a) 10% of isododecane, 40% of isohexadecane, 19% of polyethylene powder, 1% of hectorite, and 10% of black iron oxide;

or b) 35% of isododecane, 15% of isohexadecane, 10% of polyethylene powder, and 10% of iron oxide, the percentages being expressed by weight relative to the total weight of the composition.

Method of Measuring the Density of Solid Particles:

The apparent density of solid particles is measured using a Gay-Lussac pycnometer.

A precision scale (precision of 1 mg) is used and the measurements are carried out in a thermostatic chamber at 25° C. (±0.5° C.). Two reference liquids having a density d, which are demineralized water (d=1 000 kg/m³) and heptane (d=683.7 kg/m³) are also used. The density of the solid particles is measured with each reference liquid.

The pycnometer and the products used for carrying out the measurement are placed at the temperature of 25° C. The masses cited below are expressed in kilograms.

The mass M0 of the pycnometer is measured, then the pycnometer is completely filled with the reference liquid used, avoiding introducing air bubbles. The mass M1 of the filled pycnometer is measured.

A mixture of mass M2 of the material whose density d2 it is desired to measure with a mass M3 of reference liquid is then prepared. The mixture is stirred and then just before the end of stirring, the pycnometer is filled with this mixture and the mass M4 of the filled pycnometer is measured. The mass M4−M0 of the mixture present in the pycnometer is thus measured.

Since the pycnometer will have a constant filling volume, it is therefore possible to establish the following relationship:

$$(M1-M0)/d=(M2/d2+M3/d)\times(M4-M0)/(M2+M3)$$

This relationship makes it possible to calculate the value of the density d2 of the solid particles, expressed in kg/m³. A value of the density of the solid particles is thus determined for each of the reference liquids. According to the invention, the highest value (among the density measured with distilled water and the density measured with heptane) is selected as value of the density for the determination of the volume fraction of the solid particles.

Method for Measuring Retraction of a Polymer:

The principle consists in measuring, before treatment and after treatment, the length of a test piece of isolated stratum corneum and determining the percentage retraction of the test piece.

Test pieces of 1 cm×0.4 cm of stratum corneum are used which have a thickness ranging from 10 to 20 μm placed on the extensiometer MTT 610 marketed by the company DIASTRON.

The test piece is placed between 2 jaws and left for 12 hours in an atmosphere at 30° C. and 40% relative humidity.

The test piece is drawn, at the rate of 2 mm/minute, by a length of between and 10% of the initial length in order to determine the length $l_1$ from which the test piece begins to exert a force on the jaws and which is detected by the apparatus.

The test piece is then relaxed and then 2 mg of an aqueous composition containing 7% by weight of polymer are applied to the stratum corneum. After complete evaporation of water from the composition, the test piece is drawn under the same conditions as those described above in order to also determine the length $l_2$ for the treated test piece.

The percentage retraction is determined by the ratio: $100 \times (l_2-l_1)/l_1$.

The invention is illustrated in greater detail in the following non-limiting examples.

COMPARATIVE EXAMPLES 1 AND 2

A mascara composition according to the invention (Example 1) is prepared comprising:

| | |
|---|---|
| Black iron oxide (Sicovit black 85E172 from BASF) | 35 g |
| Propylene glycol | 5 g |
| Hydroxyethylcellulose (Cellosize QP4400M from Amerchol) | 1 g |
| Water | qs 100 g |

The nonvolatile fraction of this mascara contains a volume fraction of solid particles (black iron oxide) of 54% (relative to the total volume of the nonvolatile fraction) and 100% of the solid particles are first particles as defined in the present invention.

A comparative mascara composition not forming part of the invention (Example 2) was also prepared comprising:

| | |
|---|---|
| Black iron oxide (Sicovit black 85E172 from BASF) | 5 g |
| Propylene glycol | 5 g |
| Hydroxyethylcellulose (Cellosize QP4400M from Amerchol) | 1 g |
| Water | qs 100 g |

The nonvolatile fraction of this mascara contains a volume fraction of solid particles (black iron oxide) of 14.3% (relative to the total volume of the nonvolatile fraction) and 100% of the solid particles are first particles as defined in the present invention.

The curling properties of these 2 mascaras were measured according to the following protocol:

Test pieces of Caucasian hair comprising 15 hair strands of 15 mm in length having an arc of curvature having a radius of curvature of between 6 and 7 mm, were used. These test pieces are attached to a support such that the top of the test piece corresponds to the inner side of the arc formed by the test piece, the bottom of the test piece corresponding to the outer side of the arc formed by the test piece.

Before applying the mascara, the curvature of the hair test piece was measured by taking a digital profile photo using Macrozoom Navitar.

The mascara is then applied to each test piece using a brush over the bottom of the test piece. There were carried out 3 series of 10 passages of the brush with a waiting time of 2 minutes between each series of 10 passages.

20 minutes after the last passage of the brush over the test piece, the test piece of hair with make-up is photographed.

The images are processed with the Microvision image analysing system and the mean radius of curvature of the hair strands before make-up application (Rc i) and the mean radius of curvature of the hair after make-up application (Rcf) are measured, the radius of curvature being measured in millimeters.

The curling R is calculated according to the formula:

$$R = 1/Rci - 1/Rcf$$

The higher the value of R, the greater the curling of the eyelashes which is measured.

The following results were obtained:

Example 1 (invention): $R=0.010$ mm$^{-1}$

Example 2 (comparative example outside of the invention): $R=0.002$ mm$^{-1}$

It was thus observed that the curling properties of the mascara of Example 1 according to the invention are superior to those of the mascara of Example 2. A larger quantity of solid particles of black iron oxide present in the mascara makes it possible to increase the curling of the eyelashes.

COMPARATIVE EXAMPLES 3 AND 4

A mascara composition according to the invention (Example 3) was prepared comprising:

| | |
|---|---|
| Nylon-12 powder (Orgasol 2002 from Atochem) | 30 g |
| Black iron oxide (Sicovit black 85E172 from BASF) | 5 g |
| Propylene glycol | 5 g |
| Hydroxyethylcellulose (Cellosize QP4400M from Amerchol) | 1 g |
| Water | qs 100 g |

The nonvolatile fraction of this mascara contains a volume fraction of solid particles (nylon, black iron oxide) of 90% (relative to the total volume of the nonvolatile fraction) and 100% of the solid particles (nylon, black iron oxide) are first particles as defined in the present invention.

A comparative mascara composition not forming part of the invention (Example 4) was likewise prepared comprising:

| | |
|---|---|
| Carnauba wax | 30 g |
| Black iron oxide (Sicovit black 85E172 from BASF) | 5 g |
| Propylene glycol | 5 g |
| Hydroxyethylcellulose (Cellosize QP4400M from Amerchol) | 1 g |
| Surfactant (Brij 35) | 3 g |
| Water | qs 100 g |

To manufacture this mascara, an aqueous dispersion of carnauba wax was first prepared by mixing, at 95° C., 40 g of carnauba wax, 4 g of polyoxyethylenated lauryl alcohol surfactant containing 23 ethylene oxide units sold under the name "BRIJ 35" by the company UNICHEMA and 56 g of water heated to 95° C., with stirring using an Ultraturrax stirrer, until an aqueous wax dispersion having a mean particle size of about 300 nm is obtained.

75 g of the wax dispersion are then mixed with the complementary aqueous fraction comprising the other ingredients.

The nonvolatile fraction of this mascara contains a volume fraction of solid particles (carnauba wax, black iron oxide) of 84% (relative to the total volume of the nonvolatile fraction) and 3.3% of the solid particles (black iron oxide) are first particles as defined in the present invention.

The curling properties of these two mascaras were measured according to the protocol described in Examples 1 and 2 and the following results were obtained:

Example 3 (invention): $R=0.016$ mm$^{-1}$

Example 4 (comparative example outside of the invention): $R=0.012$ mm$^{-1}$

The curling properties of the mascara of Example 3 according to the invention are superior to those of the mascara of Example 4 (comparative example which is not forming part of the invention). The presence of nylon particles in place of carnauba wax particles makes it possible to improve the curling of the eyelashes.

What is claimed is:

1. A composition for coating keratinous fibres comprising, in a cosmetically acceptable medium, at least one volatile solvent and a nonvolatile fraction, said non-volatile fraction comprising:
at least one polymer capable of adhering to a keratinous material;
first solid particles comprising at least one first material chosen from crystalline and semicrystalline materials which are solid at 25° C. and have at least one of a first order phase transition, a melting transition and a combustion transition, greater than 100° C.;
and optionally second solid particles comprising at least one second material that is different from the first material, said second solid particles not being capable of coalescing at a temperature of less than or equal to 40° C.,
wherein the first solid particles and, where appropriate, the second solid particles in the composition are present in an amount such that the volume fraction of the first solid particles and, where appropriate, of the second solid particles is greater than or equal to 50% of the total volume of the nonvolatile fraction of the composition;
and, where appropriate, the volume fraction of said first solid particles is greater than or equal to 10% of the total volume fraction of said first and second solid particles,
and wherein the keratinous fibers are chosen from natural eyelashes, false eyelashes, hair, and wigs.

2. The composition according to claim 1, wherein said at least one first material has a first order phase transition that is greater than 120° C.

3. The composition according to claim 2, wherein said at least one first material has a first order phase transition that is greater than 150° C.

4. The composition according to claim 1, wherein said at least one first material has a Vicker hardness that is greater than or equal to 10.

5. The composition according to claim 4, wherein said at least one first material has a Vicker hardness ranging from 10 to 7,500.

6. The composition according to claim 4, wherein said at least one first material has a Vicker hardness that is greater than or equal to 200.

7. The composition according to claim 6, wherein said at least one first material has a Vicker hardness ranging from 200 to 7,500.

8. The composition according to claim 4, wherein said at least one first material has a Vicker hardness that is greater than or equal to 400.

9. The composition according to claim 8, wherein said at least one first material has a Vicker hardness ranging from 400 to 7,500.

10. The composition according to claim 1, wherein the at least one first material is chosen from silica, glass, diamond, copper, boron nitride, ceramics, metal oxides, micas, and polyamides.

11. The composition according to claim 10, wherein said at least one first material is chosen from iron oxides.

12. The composition according to claim 1, wherein the first solid particles have a mean size ranging from 5 nm to 50 μm.

13. The composition according to claim 12, wherein the first solid particles have a mean size ranging from 20 nm to 50 μm.

14. The composition according to claim 1, wherein the composition comprises the first solid particles and the second solid particles.

15. The composition according to claim 14, wherein the second solid particles are chosen from:
second primary solid particles, comprising at least one amorphous material having a glass transition temperature of greater than or equal to 60° C.,
second secondary solid particles, different from said second primary particles,
and mixtures thereof.

16. The composition according to claim 1, wherein the volume fraction of the first solid particles, and, where appropriate, of the second solid particles ranges from 50% to 99% of the total volume of the nonvolatile fraction of the composition.

17. The composition according to claim 1, wherein the volume fraction of the first solid particles, and, where appropriate, of the second solid particles is greater than or equal to 60% of the total volume of the nonvolatile fraction of the composition.

18. The composition according to claim 17, wherein the volume fraction of the first solid particles, and, where appropriate, of the second solid particles ranging from 60% to 99% of the total volume of the non-volatile fraction of the composition.

19. The composition according to claim 17, wherein the volume fraction of the first solid particles, and, where appropriate, of the second solid particles is greater than or equal to 70% of the total volume of the nonvolatile fraction of the composition.

20. The composition according to claim 19, wherein the volume fraction of the first solid particles, and, where appropriate, of the second solid particles ranging from 70% to 95% of the total volume of the non-volatile fraction of the composition.

21. The composition according to claim 14, wherein the volume fraction of the first solid particles is greater than or equal to 20% of the total volume fraction of the first and second solid particles.

22. The composition according to claim 21, wherein the volume fraction of the first solid particles ranging from 20% to 100% of the total volume fraction of the first and second solid particles.

23. The composition according to claim 21, wherein the volume fraction of the first solid particles is greater than or equal to 30% of the total volume fraction of the first and second solid particles.

24. The composition according to claim 23, wherein the volume fraction of the first solid particles ranges from 30% to 100% of the total volume fraction of the first and second solid particles.

25. The composition according to claim 14, wherein the second solid particles comprise second primary solid particles comprising at least one amorphous material which is solid at 25° C. and exhibits a glass transition of greater than or equal to 60° C.

26. The composition according to claim 25, wherein the second primary solid particles comprise at least one amorphous material having a glass transition temperature of greater than or equal to 80° C.

27. The composition according to claim 26, wherein the second primary solid particles comprise at least one amorphous material having a glass transition temperature of greater than or equal to 100° C.

28. The composition according to claim 25, wherein the at least one amorphous material is chosen from polymers.

29. The composition according to claim 25, wherein the at least one amorphous material is a polymer chosen from free-radical polymers and polycondensates.

30. The composition according to claim 25, wherein the at least one amorphous material is a polymer chosen from ethylene polymers, propylene polymers, acrylic polymers, acrylamide polymers, (meth)acrylonitrile polymers, polycarbonates, polyurethanes, polyesters, polyamides, polysulphones, polysulphonamides, and carbohydrates.

31. The composition according to claim 25, wherein the second primary solid particles have a mean size ranging from 10 nm to 50 μm.

32. The composition according to claim 31, wherein the second primary solid particles have a mean size ranging from 20 nm to 1 μm.

33. The composition according to claim 25, wherein the volume fraction of the first solid particles and of the second primary solid particles is greater than or equal to 10.05% of the total volume of the first and second solid particles.

34. The composition according to claim 33, wherein the volume fraction of the first solid particles and of the second primary solid particles is greater than or equal to 20.05% of the total volume of the first and second solid particles.

35. The composition according to claim 34, wherein the volume fraction of the first solid particles and of the second primary solid particles is greater than or equal to 30.05% of the total volume of the first and second solid particles.

36. The composition according to claim 35, wherein the volume fraction of the first solid particles and of the second primary solid particles is greater than or equal to 40.05% of the total volume of the first and second solid particles.

37. The composition according to claim 36, wherein the volume fraction of the first solid particles and of the second primary solid particles is greater than or equal to 50% of the total volume of the first and second solid particles.

38. The composition according to claim 15, wherein the second solid particles comprise second secondary solid particles.

39. The composition according to claim 1, wherein the at least one volatile solvent is chosen from water, volatile organic solvents, and volatile oils.

40. The composition according to claim 1, wherein the at least one polymer capable of adhering to a keratinous material is chosen from vinyl polymers, polyurethanes, polyesters, polyamides, polyureas, and cellulose polymers.

41. The composition according to claim 1, wherein the at least one polymer capable of adhering to a keratinous material is a film-forming polymer at a temperature of less than or equal to 40° C.

42. The composition according to claim 1, wherein the at least one polymer capable of adhering to a keratinous materials is a polymer capable of forming a deposit producing, at a concentration of 7% in water, a retraction of the isolated stratum corneum of more than 1% at 30° C. at a relative humidity of 40%.

43. The composition according to claim 42, wherein the retraction of the stratum corneum is of more than 1.2%.

44. The composition according to claim 43, wherein the retraction of the stratum corneum is of more than 1.5%.

45. The composition according to claim 1, wherein the at least one polymer capable of adhering to a keratinous material is present in an amount of dry matter ranging from 0.1% to 50% by weight, relative to the total weight of the composition.

46. The composition according to claim 45, wherein the at least one polymer capable of adhering to a keratinous material is present in an amount of dry matter ranging from 0.5% to 40% by weight, relative to the total weight of the composition.

47. The composition according to claim 46, wherein the at least one polymer capable of adhering to a keratinous material is present in an amount of dry matter ranging from 1% to 30% by weight, relative to the total weight of the composition.

48. The composition according to claim 1, wherein the composition further comprises an aqueous phase.

49. The composition according to claim 1, wherein the composition further comprises an aqueous phase formed of water or a mixture of water and a water-miscible organic solvent.

50. The composition according to claim 49, wherein the water-miscible organic solvent is chosen from lower monoalcohols having from 1 to 5 carbon atoms, glycols having from 2 to 8 carbon atoms, $C_3$–$C_4$ ketones, and $C_2$–$C_4$ aldehydes.

51. The composition according to claim 49, wherein the aqueous phase is present in an amount ranging from 0.1% to 98% by weight, relative to the total weight of the composition.

52. The composition according to claim 51, wherein the aqueous phase is present in an amount ranging from 1% to 80% by weight, relative to the total weight of the composition.

53. The composition according to claim 52, wherein the aqueous phase is present in an amount ranging from 5% to 65% by weight, relative to the total weight of the composition.

54. The composition according to claim 49, wherein the at least one polymer capable of adhering to a keratinous material is solubilized in the aqueous phase.

55. The composition according to claim 49, wherein the at least one polymer capable of adhering to a keratinous material is in the form of solid particles in an aqueous dispersion.

56. The composition according to claim 1, wherein the composition further comprises at least one volatile oil.

57. The composition according to claim 56, wherein the at least one volatile oil is chosen from hydrocarbon oils, silicone oils, and fluorinated oils.

58. The composition according to claim 56, wherein the at least one volatile oil is present in an amount ranging from 0.1% to 98% by weight, relative to the total weight of the composition.

59. The composition according to claim 58, wherein the volatile oil is present in an amount ranging from 1% to 65% by weight, relative to the total weight of the composition.

60. The composition according to claim 59, wherein the volatile oil is present in an amount ranging from 5% to 65% by weight, relative to the total weight of the composition.

61. The composition according to claim 1, wherein the composition further comprises a nonvolatile oil.

62. The composition according to claim 61, wherein the nonvolatile oil is present in an amount ranging from 0.1% to 50% by weight, relative to the total weight of the composition.

63. The composition according to claim 62, wherein the non-volatile oil is present in an amount ranging from 0.1% to 30% by weight, relative to the total weight of the composition.

64. The composition according to claim 63, wherein the non volatile oil is present in an amount ranging from 0.1% to 20% by weight, relative to the total weight of the composition.

65. The composition according to claim 1, wherein the at least one polymer capable of adhering to a keratinous material is solubilized or dispersed in the form of surface-stabilized particles in a liquid fatty phase.

66. The composition according to claim 1, wherein the composition further comprises a wax.

67. The composition according to claim 66, wherein the wax has a melting point ranging from 30° C. to 99° C.

68. The composition according to claim 67, wherein the wax has a melting point ranging from 45° C. to 99° C.

69. The composition according to claim 66, wherein the wax is in the form of particles having a mean size ranging from 50 nm to 50 μm.

70. The composition according to claim 69, wherein the wax is in the form of particles having a mean size ranging from 50 nm to 10 μm.

71. The composition according to claim 66, wherein the wax is present in an amount ranging from 0.1% to 50% by weight relative to the total weight of the composition.

72. The composition according to claim 71, wherein the wax is present in an amount ranging from 0.5% to 30% by weight relative to the total weight of the composition.

73. The composition according to claim 72, wherein the wax is present in an amount ranging from 1% to 20% by weight relative to the total weight of the composition.

74. The composition according to claim 1, wherein the composition further comprises a surfactant.

75. The composition according to claim 1, wherein the composition further comprises an additive chosen from colouring substances, antioxidants, fillers, preservatives, perfumes, neutralizing agents, thickeners, cosmetic active agents, sunscreens, coalescing agents, and plasticizers.

76. The composition according to claim 1, wherein the composition is a mascara.

77. The composition according to claim 1, wherein the composition does not contain:
a) 10% of isododecane, 40% of isohexadecane, 19% of polyethylene powder, 1% of hectorite, and 10% of black iron oxide; or
b) 35% of isododecane, 15% of isohexadecane, 10% of polyethylene powder, and 10% of iron oxide,
the percentages being expressed by weight relative to the total weight of the composition.

78. A method for applying make-up to keratinous fibres or a nontherapeutic treatment of keratinous fibres comprising applying to said keratinous fibres an effective amount of a composition comprising, in a cosmetically acceptable medium, at least one volatile solvent and a nonvolatile fraction, said non-volatile fraction comprising:
at least one polymer capable of adhering to a keratinous material;
first solid particles comprising at least one first material chosen from crystalline and semicrystalline materials which are solid at 25° C. and have at least one of a first order phase transition, a melting transition and a combustion transition, greater than 100° C.;
and optionally second solid particles comprising at least one second material that is different from the first material, said second solid particles not being capable of coalescing at a temperature of less than or equal to 40° C.,
wherein the first solid particles and, where appropriate, the second solid particles in the composition is present in an amount such that the volume fraction of the first solid particles and, where appropriate, of the second solid particles is greater than or equal to 50% of the total volume of the nonvolatile fraction of the composition;
and, where appropriate, the volume fraction of said first solid particles is greater than or equal to 10% of the total volume fraction of said first and second solid particles,
and wherein the keratinous fibers are chosen from natural eyelashes, false eyelashes, hair, and wigs.

79. The method according to claim 78, wherein said keratinous fibres are eyelashes.

80. A method for curling keratinous fibres comprising applying to said keratinous fibres a composition comprising, in a cosmetically acceptable medium, at least one volatile solvent and a nonvolatile fraction, said non-volatile fraction comprising:
at least one polymer capable of adhering to a keratinous material;
first solid particles comprising at least one first material chosen from crystalline and semicrystalline materials which are solid at 25° C. and have at least one of a first order phase transition, a melting transition and a combustion transition, greater than 100° C.;
and optionally second solid particles comprising at least one second material that is different from the first material, said second solid particles not being capable of coalescing at a temperature of less than or equal to 40° C.,
wherein the first solid particles and, where appropriate, the second solid particles in the composition is present in an amount such that the volume fraction of the first solid particles and, where appropriate, of the second solid particles is greater than or equal to 50% of the total volume of the nonvolatile fraction of the composition;
and, where appropriate, the volume fraction of said first solid particles is greater than or equal to 10% of the total volume fraction of said first and second solid particles,
and wherein the keratinous fibers are chosen from natural eyelashes, false eyelashes, hair, and wigs.

81. The method according to claim 80, wherein said keratinous fibres are eyelashes.

82. A method for curling keratinous fibres comprising applying to said keratinous fibres a mascara comprising, in a cosmetically acceptable medium:
first solid particles comprising at least one first material chosen from crystalline and semicrystalline materials which are solid at 25° C. and have at least one of a first order phase transition, a melting transition and a combustion transition, greater than 100° C.;
optionally second solid particles comprising a second material, different from the first material, said second solid particles not being capable of coalescing at a temperature of less than or equal to 40° C.;
at least one volatile solvent;
and a nonvolatile fraction comprising at least one polymer capable of adhering to a keratinous materials;
wherein the first solid particles and, where appropriate, the second solid particles are present in the composition in an amount such that the volume fraction of the first solid particles and, where appropriate, of the second solid particles is greater than or equal to 50% of the total volume of the nonvolatile fraction of the composition;

and, where appropriate, the volume fraction of the first solid particles is greater than or equal to 10% of the total volume fraction of the first and second solid particles, and wherein the keratinous fibers are chosen from natural eyelashes, false eyelashes, hair, and wigs.

83. The method according to claim 82, wherein said keratinous fibres are eyelashes.

84. A composition for coating keratinous fibres comprising, in a cosmetically acceptable medium, at least one volatile solvent and a nonvolatile fraction, said non-volatile fraction comprising:

first solid particles comprising at least one first material chosen from crystalline and semicrystalline materials which are solid at 25° C. and have at least one of a first order phase transition, a melting transition and a combustion transition, greater than 100° C.;

and optionally second solid particles comprising at least one second material that is different from the first material, said second solid particles not being capable of coalescing at a temperature of less than or equal to 40° C., wherein the first solid particles and, where appropriate, the second solid particles in the composition are present in an amount such that the volume fraction of the first solid particles and, where appropriate, of the second solid particles is greater than or equal to 50% of the total volume of the nonvolatile fraction of the composition;

and, where appropriate, the volume fraction of said first solid particles is greater than or equal to 10% of the total volume fraction of said first and second solid particles, and wherein at least a portion of at least one of said first solid particles and said optional second solid particles are chosen from at least one polymer capable of adhering to keratinous fibers, and wherein the keratinous fibers are chosen from natural eyelashes, false eyelashes, hair, and wigs.

* * * * *

UNITED STATES PATENT AND TRADEMARK OFFICE
CERTIFICATE OF CORRECTION

| | |
|---|---|
| PATENT NO. | : 7,211,244 B2 |
| APPLICATION NO. | : 10/195430 |
| DATED | : May 1, 2007 |
| INVENTOR(S) | : Frédéric Auguste et al. |

It is certified that error appears in the above-identified patent and that said Letters Patent is hereby corrected as shown below:

In claim 18, column 20, line 27, "ranging" should read --ranges--.

In claim 20, column 20, line 37, "ranging" should read --ranges--.

In claim 22, column 20, line 45, "ranging" should read --ranges--.

In claim 42, column 21, line 57, "materials" should read --material--.

In claim 64, column 23, line 6, "non volatile" should read --non-volatile--.

In claim 82, column 24, line 64, "materials;" should read --material;--.

Signed and Sealed this

Twenty-fourth Day of July, 2007

JON W. DUDAS
*Director of the United States Patent and Trademark Office*